United States Patent [19]
Cohen

[11] Patent Number: 5,830,919
[45] Date of Patent: Nov. 3, 1998

[54] METHOD TO PROTECT PLANTS FROM FUNGAL INFECTION

[75] Inventor: Yigal Cohen, Kiryat Ono, Israel

[73] Assignee: Agrogene Ltd., Kiryat Ono, Israel

[21] Appl. No.: 658,636

[22] Filed: Jun. 5, 1996

Related U.S. Application Data

[63] Continuation of PCT/US94/14,108, Dec. 9, 1994.

[30] Foreign Application Priority Data

| Dec. 12, 1993 | [IL] | Israel | 107992 |
| Apr. 28, 1994 | [IL] | Israel | 109474 |
| Nov. 30, 1994 | [IL] | Israel | 111824 |

[51] Int. Cl.⁶ .................................................. A01N 37/44
[52] U.S. Cl. ......................... 514/561; 514/538; 514/551; 514/563
[58] Field of Search ................................... 514/561, 558, 514/562, 563, 564, 567, 489

[56] References Cited

U.S. PATENT DOCUMENTS

| 3,899,585 | 8/1975 | Misato et al. | 424/274 |
| 3,991,208 | 11/1976 | Dudzinski et al. | 424/319 |
| 4,481,219 | 11/1984 | Watkinson | 424/319 |
| 5,096,700 | 3/1992 | Seibel et al. | 424/52 |

FOREIGN PATENT DOCUMENTS 1048507  11/1965  United Kingdom .

OTHER PUBLICATIONS

Y. Cohen; 3–Aminobutyric Acid Induces Systemic Resistance Against Peronospore Tabacina; Physiological and Molecular Plant Pathology (1994) 44, 273–288.

Fungicides an Advanced Treatise; Chemistry and Physiology, vol. II, 1969; p. 549–551, 573, 577. Torgeson.

Y. Cohen; Local and Systemic Control of Phytophthora Infestans in Tomato Plants by DL–3–Amino–N–Butanoic Acids; The American Phytopathological Society, vol. 84, No. 1, 1993, pp. 55–59.

Y. Cohen et al; Systemic Translocation of ¹⁴C–DL–3Aminobutyric Acid in Tomato Plants in Relation to Induced Resistance Against Phytophthora Infestans; Physiological & Molecular Plant Pathology, (1994) 45, 441–456.

Y. Cohen et al; Beta–Aminobutyric Acid Induces the Accumulation of Pathogenesis–Related Proteins in Tomato (*Lycopersicon Esculentum* L.) Plants . . . ; Plant Physiol. (1994) 104: 59–66.

A.J.P. Oort et al; Aspects of Chemotherapy; Laboratory of Phytopathology, Agricultural University; 1960, pp. 981–992.

J. Li et al; Induction of Resistance of Cotton Plants . . . and Methyl Jasmonate; Journal of Plant Diseases and Protection, vol. 103(3), 288–299, 1996.

G. C. Papavizas et al; Effect of Amino Compounds and Related Substances Lacking Sulfur . . . of Peas; Phytopathology, vol. 53, pp. 116–122, 1963.

J. Y. Sunwoo et al; Induced Resistance Against Phytophthora Capsici . . . Acid; European Journal of Plant Pathology, vol. 102, 1996, pp. 663–370.

O.M. van Andel; Investigation of Plant Chemotherapy–II. Influence of Amino Acids on the Relation Plant Pathogen; T. Plzickten 64 (1958): pp. 307–327.

G. C. Papavizas; Comparison of Treatments Suggested for Control of Aphanomyces Root Rot of Peas; Plant Disease Reporter; vol. 51, No. 2, (1967), pp. 125–129.

W. A. Ayers et al; An Exocellular Pectolytic Enzyme of Aphanomyces Euteiches; Phytopathology; 55:125–248; 1965; pp. 249–253.

Mode of Action of L–Threo–Beta–Phenylserine as a Chemotherapeutant . . . ; Nature, vol. 211, pp. 326–327; 1966.

G. C. Papavizas; Greenhouse Control of Aphanomyces Root of Peas . . . Acid; Plants Disease Reporter; vol. 48, No. 7; 1964, pp. 537–541.

G. C. Papavizas et al; Effect of Sulfur–Containing Amino Compounds and Related Substances . . . of Peas; Phytopathology, vol. 53, pp. 109–115; 1963.

*Primary Examiner*—Allen J. Robinson
*Attorney, Agent, or Firm*—Browdy and Neimark

[57] ABSTRACT

A method for protecting a crop against fungal diseases by inducing local and systemic resistance of the crop comprising applying to the crop or its locus a composition containing an effective amount of a β-aminobutyric acid or β-amino valeric acid and derivatives thereof.

37 Claims, No Drawings

METHOD TO PROTECT PLANTS FROM FUNGAL INFECTION

This is a continuing application of PCT/U.S. Pat. No. 94/14,108, filed Dec. 9, 1994.

INTRODUCTION

The present invention concerns a novel method to protect plants from pathogenic attack. The present invention more particularly concerns a method of applying selected non-fungicidal compounds and compositions to a crop and its locus to immunize, vis. induce local and systemic resistance of the crop against fungal diseases, wherein such action is referred to in this application as "induced plant defence" (hereinafter IPD). Such compounds lacks any anti-fungal activity when applied directly to the fungus but when applied to a crop they enhance its own immunization capacity via altering its metabolism.

BACKGROUND OF THE INVENTION

IPD (also known as SAR, Systemic Aquired Resistance) in a crop results from altered metabolism of plant tissue and, is manifested by various defense mechanisms including the accumulation in the crop of soluble proteins referred to as pathogenesis-related (PR) proteins. Some PR proteins have been shown to be hydrolytic enzymes such as chitinases and β-1, 3-gluconases, while others are shown to be peroxidases. Also accumulated are a group of these proteins having a molecular weight or about 10 to 20 kDaltons referred to as P14 proteins, which are now known to be anti-fungal. All or part of these proteins are believed to participate in the defense system of a crop. Various isonicotinoyl-pyridinyl-hydrazine-derivatives such as 2,6,- dichloroisonicotinic acid (INA), and benzothiadiazole compounds such as Ciba-Geigy CGA 245704) have been described in the patent literature as immunizing healthy plants against fungal diseases (European Patent Publication Numbers 268 775, 0 288 976; and 313 512). The use of threo-DL-β-methylaspartic acid and of DL-β-aminobutyric acid for the control of root rot of peas caused by *Aphanomyces euteiches* Drechs, has also been described (Papavizas, Plant Disease Reporter, 48, 537–541 (1964), Papavizas, Plant Disease Reporter, 51, 125–129 (1967).

The use of D-alanine, D- and DL leucine and DL-β-aminobutyric acid at 0.3M was described to reduce scab in apple caused by *Venturia inaequalis* (Kuc et al., 49: 313–315, 1959). Van Andel, showed (Tijdschur, Plantenziekten, 64: 307–327, 1958) that DL-serine, D-serine (and to a lesser extent L-serine), phenylserine, DL-threonine but not DL-α-aminobutyric acid nor DL-βaminobutyric acid behaved as chemotherepeutants against the fungus Cladosporium cucumerinum on cucumber (Ibid, page 318). Oort and Van Andel (1960, Mededel.

Landsborowhager school Dpzoekingssta. Staat Gent 25: 981–992) showed that DL-β-aminobutyric acid applied to leaves of tomato protected those leaves against *Phytophthora infestans* (page 987).

Various derivatives of DL-β-aminobutyric acid and β-aminocrotonic acid have been described in the patent literature as fungicides against *Phytophthora infestans* in tomato and *Plasmopara viticola* in grapes (German Patent NO. 1,120,802).

Recently, Cohen, Niderman, Mosinger and Fluhr (Plant Physiol. 1994, 104: 58–66) reported that PR proteins are involved in IPD in tomatoes.

Systemic acquire resistance is very often specific to a crop and a disease. For example INA and CGA 245704 can immunize tobacco against the fungus *Peronospora tabacina* but not potato nor tomato against *P. infestans* (Y. Cohen, unpublished). Also known in the literature is that various isomers of a compound may show different abilities to induce systemic resistance. For example, DL-β-aminobutyric acid induces resistance against Fusarium wilt in tomato whereas α-aminoisobutyric acid induces resistance against powdery mildew in wheat (Kalix et al, in Modern Fungicides and Antifungal Compounds, eds. Lyr, Russel and Sissler Intercept 1995). The literature also teaches that even enantiomers of the same molecule greatly differ in their IPD ability. Thus Cohen showed (Physio Molecular Plant Pathol. 44: 273–288, 1994) that (R)-β-aminobutyric acid can immunize tobacco against *P. tabacina* whereas (S–)-β-aminobutyric cannot. Oort and Van Andel (Ibid) concluded:. "We do not understand why one of two related amino acids has an evident effect and the other has not, and why one influences a given plant pathogen combination but has no or hardly any influence on another" (Ibid page 987).

The method of the present invention is not obvious in view of the prior art cited, for the following reasons:

1. Oort and Van Andel (Mededel Landbourhoogeschool Opzockkinssta. Staat Gent 25: 981–992, 1960) showed that BABA (DL-β-aminobutyric acid) applied exclusively to the leaves of tomato 2 days before inoculation reduced infection with *P infestans* (Ibid page 987 line 5). The present invention shows that BABA protects plants against disease when applied to either the leaves or to the roots, or even injected to the stem, and may be applied either before or after inoculation. Also data of OOrt and Van Andel are merly qualitative as no BABA concentration nor percent protection are given.

2. U.S. Pat. No. 3,899,585 (Misato et al) Aug. 12, 1975 teaches in Table 1 that test compound NO. 13 (which is the closest to the present invention) 2-aminobutyric acid lauryl ester hydrochloride applied to rice leaves reduces rice blast disease. The present invention teaches that 2-aminobutyric acid was totally ineffective in reducing diseases in various crops (see Cohen Phytopathology 83: 55–59, 1994, Cohen, Physiol. Molecul. Plant Pathol. 44: 273–288-1994). Also it teaches that test compound NO. 13 should be applied preventively rather than curatively, unlike the present invention which allows application of the test compound curatively. Interestingly enough test compound NO. 13 is probably inactive in cucumber against downy mildew as it is missing from Example 4 (Table 4) unlike the present invention showing that BABA is active against this disease.

3. U.S. Pat. No. 3,991,208 (Dudzinzki et al) Nov. 9, 1976 teaches that a tertiary amine group attached to a 2-carbon of a long chain alkyl, and carboxyethyl group substituent of the nitrogen atom are surface active compounds that are antibacterial (against Gram positive bacteria). Such compounds are not amino acids, have no effect on fungi and do not control fungal plant diseases either directly or indirectly and therefore have no relevance to the present invention.

4. U.S. Pat. No. 481,219 (Watkinson) Nov. 6, 1984 teaches that timber decay due to fungal attack by mainly Basidiomycetes may be prevented by a composition containing a nitrogenous compound and a sacharide compound. The nitrogenous compound selected from a group consisting DL-methionine sulfoxide, 5-hydroxy lysine HCl, and aminoisobutyric acid. The latter compound is (CH3)2 C(NH2) COOH (Column 2 line 28) which is 2-amino-iso butyric acid. According to the present invention this compound is not suitable for inducing systemic resistance against fungal plant pathogens, but BABA does, not to say that the present invention deals with protection of alive green plants and not of a dead woody tissue like timber. Moreover, according to Watkinson the composition must contain a sugar as an energy source for the fungus, whereas the present invention does not.

5. U.S. Pat. No. 5,096,700 (Seibel et al) Mar. 17, 1992 teaches that halogenated amino acid derivatives are useful antibacterial agents in humans. This prior art is indeed not relevant to the present invention because first it deals with bacterial human diseases and not in fungal diseases of crop plants; second it involves halogenated (at least one halogen atom bound to the carbon backbone at position 2) amino acids, which is not required to BABA to induce IPD;

6. GB, 1,048,507, (Harinack et al) Nov. 16, 1965 teaches that glycine derivatives are effective systemic fungicides in crop plants although they are not effective against fungus spore germination in in-vitro tests (page 1 line 40).

This prior art depart from the present invention due to the fact that glycine is a 2-amino acid ($\beta$-amino acid) in which the NH2 group is bonded to carbon 2, while the present invention deals with 3-amino acids ($\beta$-amino acids) in which the NH2 group is bound to carbon 3. According to the present invention only 3-aminobutyric acids, but not 2-aminobutyric acids, have systemic IPD effect.

The present invention deals with compounds that protect crop plants against fungal attack via immunization, namely altering plant metabolism so as it can resist fungal colonization in its tissues. It was shown by Cohen et al (Plant Physiology 104: 59–66 1994) that BABA enhances the accumulation of PR-proteins in tomato. This accumulation was correlated with resistance to *P. infestans*. However, this is probably not the case in other crops such as curcurbits and tobacco in which BABA also induces IPD response. In curcubits BABA induces the accumulation of callose and lignin in the infected sites which probably stop the fungus whereas in tobacco the IPD mechanism remains obscure (Cohen, Physiol. Molecule Plant. Pathol 44: 273–288, 1994).

OBJECTIVES OF THE INVENTION

It is the objective of the present invention to provide a novel method to induce IPD. It is a further objective of the present invention to provide a novel method to induce IPD in selected crops.

SUMMARY OF THE INVENTION

We have found a novel method of protecting a crop against fungal diseases caused by fungi by applying to the crop or its locus a composition containing an effective amount of a compound of formula (I):

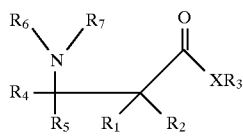

$R_1$ and $R_2$ are independently hydrogen, $C_{1-8}$ alkyl, phenyl, and phenyl $C_{1-4}$ alkyl $R_3$ is hydrogen; $C_{1-23}$ alkyl; carboxy $C_{1-4}$ alkyl; phenyl $C_{1-4}$ alkyl; wherein the phenyl moiety is unsubstituted or monosubstituted by halogen; or $C_{2-23}$ alkoxy-carbonyl $C_{1-4}$alkyl;

$R_4$ and $R_5$ are independently hydrogen or $C_{1-8}$ alkyl;

R6 and R7 are independently hydrogen; C1–8 alkyl C2–8 alkanoyl; phenyl C1–4 alkyl, benzoyl wherein the phenyl moiety is unsubstituted or monosubstituted by halogen; C2–8 alkoxy-carbonyl; CONHR8 wherein R8 is is hydrogen, C1–8 alkyl, phenyl, phenyl C1–4 alkyl; phenyl C2–4 alkyloxycarbonyl;

X is O, S or N, and salts thereof; and the crop is selected from the group consisting of corn, cucumber, melon, broccoli, cauliflower, kohlrabi, potatoes, cabbage, sunflower, tobacco, grapes, cotton, maize, sorghum, pearl miller, rice, lettuce, hop, avocado, citrus, soybean, and onions.

DETAILED DESCRIPTION OF THE INVENTION

Alkyl as used herein refers to straight chains, branched and cyclic forms and preferably contain one to four carbon atoms.

R1 and R2 are preferably independently hydrogen, methyl or phenyl, more preferably R1 is hydrogen or methyl and R2 is hydrogen.

R3 is preferably hydrogen.

R4 and R5 are preferably independently hydrogen or C1–3 alkyl, more preferably R4 is hydrogen or methyl and R5 is hydrogen or C1–3 alkyl, more preferably R4 is hydrogen or methyl and R5 is hydrogen.

R6 and R7 are preferably independently hydrogen, C1–6 alkyl, benzyl optionally substituted by halogen, more preferably R6 is hydrogen or methyl and R7 is hydrogen.

X is preferably oxygen.

Preferred compounds of the invention are the $\beta$-aminobutyric acids and the $\beta$-aminovaleric acids; and most preferred is R-$\beta$-aminobutyric acid. The structures of various aminobutyric acids are shown in Scheme 1.

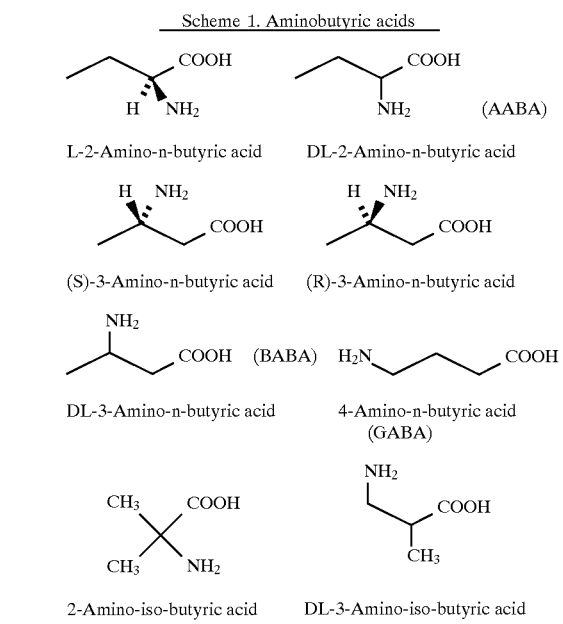

Salt forms of the compound of formula (I) contemplated in this application include acid addition salts such as those obtained by the addition of $HCl$, $CF_3CO_2H$, toluene sulfonic acid, methane sulfonic acid and $(CO_2H)_2$

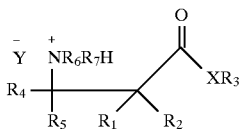

wherein Y is the residue of the acid;
alkali metal salts such as those obtained by treatment with NaOH, KOH or LiOH

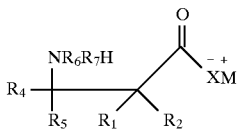

wherein M is an alkali metal such as Na, K or Li; and acid addition/amine salts such as those obtained by treatment with HCl and an amine such as diethylamine, propyl amine, benzylamine.

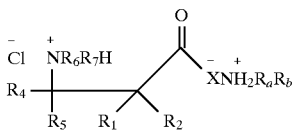

wherein $R_a$ and $R_b$ are substituents.

Preferred crops in which the method of the present invention is applicable are cucumbers, melon, broccoli, cauliflower, kohlrabi, potatoes, sunflower, tobacco, grapes, cotton, maize, sorghum, cabbage, pearl millet, rice, onion and hop. Most preferred are sunflower, grapes, cucumber, melon, broccoli, kohlrabi, cauliflower, potatoes, tobacco and maize.

Production methods

The novel compounds encompassed by the present application are structurally related to known compounds and can be easily prepared by either derivatising the known compounds or by modifying the procedures for preparing the known compound, as required. These procedures will be apparent to those skilled in the art. The following procedures are illustrative.

Compounds of the formula (Ia)

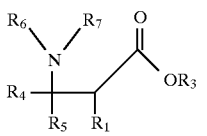

wherein $R_1$ and $R_{4-7}$ are as previously defined and $R_3$ represents hydrogen or $C_{1-8}$ alkyl can be obtained from a compound of the formula (IIa).

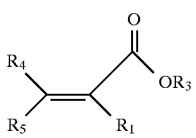

To prepare compounds of formula (Ia) where $R_6$ is H and $R_7$ is as previously defined, the compound of formula (IIa) is reacted with $NR_7H_2$, wherein $R_7$ is as previously defined. Reactions of this type are described in the literature, e.g., by A. Zilkha and J. Rivlin, J. Org. Chem. 1957, 23, 94.

To prepare compounds of formula (Ia) where $R_6$ and $R_7$ are as previously defined but excluding hydrogen, the compound of formula (IIa) is reacted with $NR_6R_7Li$, wherein $R_6$ and $R_7$ are as previously defined but excluding hydrogen. Reactions of this type are described in the literature, e.g., by Davies et al., Tetrahedron: Asymmetry, Vol. 2, No. 3, pp. 183–186 (1991).

Compounds of the formula (IIa) are either known or obtainable from known compounds according to standard procedures.

As can be appreciated, in such cases where $R_4$ and $R_5$ do not represent, the same substituent, the carbon atom to which they attach is chiral. Procedures for preparing each enantiomer form are either specifically described in the literature, e.g., in EP 0 144 980 or in Davies, supra, or can be prepared according to analogous procedures.

The present method was found to be effective against a variety of diseases. Examples are late blight, downy mildew, blue mold, leaf spots, fusarium wilt, trunk rot, fruit brown rot, damping off, white rust, black shunk and Phytophthoras root rots.

The compounds of this invention will typically be applied to crops or their locus before or after the onset or after the initial signs of fungal attack and may be applied to the foliar surfaces of the crop. The amount of the active ingredient to be employed will be sufficient to induce the systemic resistance of the crop to control the fungi and will vary depending on such factors as the species of fungi to be controlled, the type of treatment (for example, spraying dusting, seed treatment, soil drench), the condition of the crop, and the particular active ingredient used.

As an application to the corp or its locus, the compounds will be applied to the crops with a dosage rate of from 0.1 to 5 kg/ha, preferably from 0.2 to 2 kg/ha, with application being repeated as necessary, typically at intervals of every one to three weeks.

Depending on circumstances, the compounds of this invention may be used in association with other pesticides, e.g., fungicides, insecticides, acaricides, herbicides, or plant growth regulating agents in order to enhance their activity or to widen their spectrum of activity.

The compounds of this invention are conveniently employed as fungicidal compositions in association with agriculturally acceptable carriers or diluents. Such compositions also form part of the present invention. They may contain, aside from a compound of formula (I) as active agent, other active agents, such as fungicides. They may be employed in either solid or liquid application forms e.g., in the form of a wettable powder, an emulsion concentrate, a water dispersible suspension concentrate ("flowable"), a dusting powder, a granulate, a delayed release form incorporating conventional carriers, diluents and/or adjuvants. Such compositions may be produced in conventional manner, e.g. by mixing the active ingredient with a carrier and other formulating ingredients.

Particular formulations to be applied in spraying forms such as water dispersible concentrates or wettable powders may contain surfactant such as wetting and dispersing agents, e.g., the condensation product of formaldehyde with naphthalene sulphonate, an alkyl-aryl-sulphonate, a lignin sulphonate, a fatty alkyl sulphate an ethoxylated alkylphenol and an ethoxylated fatty alcohol.

In general, the formulations include from 0.01 to 90% by weight of active agent, said active agent consisting either of at least one compound of formula (1) or mixture thereof with other active agents, such as fungicides. Concentrate forms of compositions generally contain between about 2 and 80%, preferably between about 5 and 70% by weight of active agent. Application forms of formulation may, for example, contain from 0.01% to 20% by weight, preferably from 0.01% to 5 % by weight, of active agent.

Formulation Example I: Wettable powder 50 parts by weight of a compound of formula (I) are ground with 2 parts of lauryl sulphate, 3 parts sodium lignin the sulphonate and 45 parts of finely divided kaolininite until the mean particle size is below 5 microns. The resulting wettable powder so obtained is diluted with water before use to a concentration of between 0.01% to 5% active ingredient. The resulting spray liquor may be applied by foliar spray as well as by root drench application.

Formulation Example II: emulsion concentrate 25 parts by weight of a compound of formula I, 65 parts of xylene, 10 parts of the mixed reaction product of an alkylphenol with xyleneoxide and calcium-dodecyl-benzene sulphonate are thoroughly mixed until a homogeneous solution is obtained. The resulting emulsion concentrate is diluted with water before use.

Formulation Example III: Granulate (for soil treatments)

Onto 94.5 parts by weight of quartz sand in a tumbler mixer is sprayed 0.5 parts by weight of a binder (non-ionic tenside) and is thoroughly mixed. 5 parts by weight of compound of the formula (I) in powdered form are then added and thoroughly mixed to obtain a granulate formulation with a particle size in the range of from about 0.3 to about 0.7 mm. The granulate may be applied by incorporation into the soil adjacent the plants to be tested.

Formulation Example IV: Seed or Tuber Dressing 25 parts by weight of compound of the formula (I), 15 parts of dialkylphenoxy-poly-(ethylenoxy) ethanol, 15 parts of fine silica, 44 parts of fine kaolin, 0.5 parts of a colorant (e.g., crystal violet) and 0.5 parts of xantham gum are mixed and ground in a contraplex mill at approximately 10,000 rpm to an average particle size of below 20 microns.

The resulting formulation is applied to the seeds or tubers as an aqueous suspension in an apparatus suitable for that purpose. Where the compound of the formula (I) is liquid, it is first absorbed on the carriers, if desired with the air of a small amount of a volatile solvent such as acetone. The resulting powder is first allowed to dry if a solvent is used, then the other ingredients are added and the rest of the procedure is carried out.

Formulation Example V: Soil Drench Drip Irrigation 2 parts by weight of compound of the formula (I) are dissolved in 1,000 parts of water. The resulting formulation is applied to plants by drip irrigation.

As previously mentioned, the compounds of formula (I) are effective in activating or enhancing a crop's defense system against fungal diseases caused by fungi. Such activity can be demonstrated in using the general procedures of the following tests:

Test A: IPD in potato plants against *Phytophthora infestans*. Potato plants (cultivar Bintje) are grown from tubers in pots filled with sandy loam, peat and perlite mixed in equal volumes, in the greenhouse (20°–22° C.). The plants are ready for testing when they have 6 or 7 compound leaves.

Tests are carried out with the metalaxyl-resistant isolate MR1 of *Phytophthora infestans*, as well as the MS2, MS3, MR2 and MR3 isolates (Kadish and Cohen, Phytopathology, 78: 912–9155 1988). The fungus is grown on potato tuber slices at 15° C. in the dark. Fresh sporangia are harvested at 6 days after inoculating the slices into double distilled water (4° C.) and their concentration adjusted to 10,000 sporangia/ml before used for challenge inoculations.

The compounds of this application are dissolved in water and sprayed on either the lower or upper leaf surfaces of the potato plants with a fine atomizer (about 10 ml per plant). The plants are left on the bench until the droplets dry and then are placed in a growth cabinet calibrated to 20° C. and 14 hours of light per 10 day.

Challenge inoculation with *P. infestans* is carried out at time intervals ranging from 30 minutes to 12 days after treatment with the compounds, by spraying a sporangial suspension on the upper leaf surfaces (about 15 ml per plant). In one experiment, inoculum droplets (10 containing about 100 sporangia) are placed on the leaf surfaces, two droplets per leaflet, one on each side of the main vine. In another experiment the compounds are applied curatively, 24 hours after inoculation with *P. infestans*.

Inoculated plants are kept at 100% RH in the dark for 24 hours at 18° C. and then returned to a growth cabinet maintained at 20° C. with 12 hours light per day. Disease severity is monitored 4–8 days after inoculation by visually estimating the proportion or a leaf area covered by blight lesions.

Test B: IPD in tobacco plants against *Peronospora tabacina*. Tobacco plants (cultivars Ky-14 or Ky-16) are grown from seek in pots in the greenhouse. When reaching the 10-leaf stage or older the compounds of this application are injected into the stem of the plant. At 1–3 days before injection or at 1–10 days after injection plants are challenge-inoculated with conidia of the fungus *Peronospora tabacina* Adam which causes the blue mold disease. Conidia are harvested from previously infected tobacco plants. Inoculation is done with 10,000–100,000 conidia/ml, with approximately 50 ml per plant. The procedure described above for inoculation, maintaining and scoring the disease are also applicable here.

While the invention will now be described in connection with certain preferred embodiments in the following examples, it will be understood that it is not intended to limit the invention to these particular embodiments. On the contrary, it is intended to cover all alternatives, modifications and equivalents as may be included within the scope of the invention as defined by the appended claims. Thus, the following examples, which include preferred embodiments, will serve to illustrate the practice of this invention, it being understood that the particulars shown are by way of example and for purposes of illustrative discussion of preferred embodiments of the present invention only and are presented in the cause of providing what is believed to be the most useful and readily understood description of procedures, as well as of the principles and conceptual aspects of the invention.

EXAMPLES

EXAMPLE 1: N-(2-hydroxyethyl)-aminobutyric acid

A solution of 86 g of crotonic acid (1 mole) and ethanolamine (1 mole) in pyridine (200 ml) is refluxed for 2–3 hours and subsequently cooled. The resulting produce is filtered and recrystallized to yield the title compound having m.p. 178°–180° C. (compound 1.1, Table 1). Following analogous procedure, the compounds 1.2–1.7, 1.10, 1.11, and 1.13–1.15 set forth in Table 1 are obtained.

EXAMPLE 2: 3-aminohexanoic acid

A mixture of 2 hexenoic acid (7.0 g, 0.06 mol) and concentrated aqueous ammonium hydroxide (70 ml) is heated for 24 hours in an autoclave at 150° C. The cooled mixture is treated with carbon black and filtered. After evaporation of the solvent the crude product is recrystallized from ethanol to give the title compound m.p. 203° C. (compound 1.21, Table 2). Following an analogous procedure, the compounds 1.8, 1.9, 1.12 and 1.18–1.20 of Table 1 are obtained.

EXAMPLE 3: N-benzoyl-3-aminobutyric acid

To a cooled solution of 3-aminobutyric acid (13 g) in 2M NaOH (130 ml) is added benzoyl chloride (19.7 g) over the course of two hours. The mixture is allowed to warm to room temperature. Washing with diethyl ether, acidifying of the aqueous phase with 20% HCl, extraction with diethyl ether, drying over $MgSO_4$, evaporation of the solvent and recrystallization in ether/hexane gives the title compound m.p. 150°–152° C. (compound 1.16, Table 1).

EXAMPLE 3A; DL-N-benzoyl-3-aminobutyric acid n-octyl-ester

To 3.0 r DL-N-benzoyl-3 -aminobutyric acid in 30 ml Dichloro methane, was added 3.0 g PC15 in small portions, keeping the mixture temperature at 5° C. The mixture was allowed to warm to 22°–20° C. and stirred during 5 hr. Petrol ether 60–80 (150 ml) was added, the chloride was filtered and dried, yielding 2.3 g product.

To the chloride in 20 ml Dichloroethane was added 4.1 g. n-octanol in 10 ml Dichloroethane, during 10 minutes at 20° C. The mixture was heated to 65° C. during 6 hr. After distillation, 20 ml Dichloroethane was added and washed with 3×10 ml sodium bicarbonate (2%) dried over $MgSO_4$. Evaporation of the solvent gave 2.0 g of the titled compound having a molecular weight of 319.

Following an analogous procedure, compound 1.17 of Table 1 is obtained.

TABLE 1

COMPOUNDS PREPARED OF THE FORMULA:

$$R_4 \overset{NHR_6}{\underset{R_5 \ R_1}{|}} \overset{O}{\overset{\|}{C}} OH$$

| Cpd | $R_1$ | $R_4$ | $R_5$ | $R_6$ | m.p.(°C.) |
|---|---|---|---|---|---|
| 1.1 | H | $CH_3$ | H | hydroxyethyl | 178–180 |
| 1.2 | H | $CH_3$ | H | isopropyl | 167–169 |
| 1.3 | H | $CH_3$ | H | benzyl | 178–180 |
| 1.4 | H | $CH_3$ | H | cyclohexyl | 161–163 |
| 1.5 | H | $CH_3$ | H | n-hexyl | 151–153 |
| 1.6 | H | $CH_3$ | H | p-chlorobenzyl | 152–154 |
| 1.7 | H | $CH_3$ | H | benzyl | 180–182 |
| 1.8 | H | ethyl | H | H | 128–130 |
| 1.9 | H | $CH_3$ | $CH_3$ | H | 216 |
| 1.10 | $CH_3$ | H | H | benzyl | 148 |
| 1.11 | H | $CH_3$ | H | phenyl-ethyl | 164 |
| 1.20 | H | phenyl | H | H | 220–221 |
| 1.13 | H | $CH_3$ | H | n-octyl | 150 |

TABLE 1-continued

COMPOUNDS PREPARED OF THE FORMULA:

$$R_4 \overset{NHR_6}{\underset{R_5 \ R_1}{|}} \overset{O}{\overset{\|}{C}} OH$$

| Cpd | $R_1$ | $R_4$ | $R_5$ | $R_6$ | m.p.(°C.) |
|---|---|---|---|---|---|
| 1.14 | H | $CH_3$ | H | n-decyl | 148 |
| 1.15 | H | ethyl | H | benzyl | 157–160 |
| 1.16 | H | $CH_3$ | H | benzoyl | 150–152 |
| 1.17 | H | $CH_3$ | H | benzyloxycarbonyl | 128–130 |
| 1.18 | H | ethyl | H | H | 178–180 |
| 1.19 | H | $CH_3$ | H | H | 209–210* |
| 1.20 | H | $CH_3$ | H | $CH_3$ | 86–87** |
| 1.21 | H | propyl | H | H | 203 |

*(R) - enantiomer
**monohydrate

EXAMPLE 4: N-benzyloxycarbonyl-3-aminobutyric acid (4-chlorophenyl)-1-ethylamide Z-protected β-aminobutyric acid (0.02 ml), (4-chlorophenyl)-1-ethylamine and 1.1 equivalents of DCC (dicyclohexyl carbonimide) are stirred in ethyl acetate at room temperature for 16 hours. The precipitate is filtered, the filtrate evaporated and chromatographed on silica gel (hexane/ethyl acetate 1:1) to give the title compound as a mixture of diastereomers m.p. 168°–178° C.

EXAMPLE 5: β-aminobutyric acid hydrochloride 5.15 g β-aminobutyric acid (50 mol) are dissolved in 650 ml methanol. After addition of 5.5 ml concentrated HCl the solution is evaporated. The residue is triturated in diethyl ether, decanted and dried. A colorless oil is isolated. Microanalysis: C, 34.4; H, 7.2; N, 10.0; Cl, 25.4

EXAMPLE 6: β-aminobutyric acid sodium salt 2.06 g β-aminobutyric acid (20 mol) are dissolved in 100 ml of a mixture of water:methanol (1:1). One equivalent NaOH in 10 ml water is added. The solution is evaporated and the resulting amorphous solid is dried. Microanalysis: C, 37.4; H, 6.7; N, 10.9.

EXAMPLE 7: β-aminobutyric acid diethylammonium chloride 1.4 g β-aminobutyric acid (10 mol) are dissolved in 100 ml of methanol. Diethylamine (0.9 g, 12.3 mol) is added and the residue is evaporated. The oily residue is washed with ether, decanted and dried to afford an amorphous material, H-NMR ($CD_3$ OD, 200 MHz) 1.29 (m, 9H, 3 $CH_3$; 2.25–2.45 (m, 2H, $CH_2$); 3.14 (p, 4H, $CH_2$ $CH_3$); 3.34–3.58 (m, 1H,CH)

EXAMPLE 8: Protection of tomato plants against fusarium wilt

Tomato plants were grown in sterile soil in the greenhouse. When they reached the 4-leaf stage they were treated with compound of the formula (I) solution by a soil drench. Four days later the plants were uprooted, washed with water and their root system immersed for two minutes in conidial suspension ($10^7$ conidia/ml) of the fungus *Fusarium oxysporum* f.sp. *lycopersici*. Plants were then transplanted (without washing) in pots filled with sterile soil. Twelve days later all challenged—control plants wilted of the disease whereas none of the challenged treated plants wilted. Growth of the latter plants was similar to that of control, unchallenged-uninoculated plants. Results are shown in Table 2.

EXAMPLE 9:

Following the method of Example 8, a similar experiment was run using lower concentration of BABA. The results are shown in Table 3.

TABLE 2

Protection of tomato plants (cv. Rehovot - 13) against fusarium wilt caused by *Fusarium oxysporum* f. sp. *lycopersici* by aminobutyric acids (soil drench)

|  | Percent of plants | |
| --- | --- | --- |
| Compound | Healthy | Wilted |
| None | 0 | 100 |
| AABA | 34 | 66 |
| BABA | 100 | 0 |
| GABA | 7 | 93 |

Plants were soil-drenched with 2000 ppm of the compound and inoculated 4 days later; rating was taken 12 days after inoculation.

TABLE 3

Protection of tomato plants (cv. Rehovot - 13) against fusarium wilt caused by *Fusarium oxysporum* f. sp. *lycopersici* by lower concentrations of BABA (soil drench)

| Concentration O (ppm) | Percent Wilted Plants |
| --- | --- |
| 0 | 100 |
| 250 | 53 |
| 500 | 43 |
| 1000 | 0 |

EXAMPLE 10:

Following the above described methods, the effect of aminobutyric acids on downy mildew in sunflower was studied. The results appear in Table 4, which shows the marked activity of BABA in percent protection.

EXAMPLE 11:

Following the above described methods, the effect of aminobutyric acids on *Plasmopara viticola* in grape plants were studied. The results which appear in Table 5, show the good protection given by BABA.

EXAMPLE 12:

Following the above described methods, the effect of aminobutyric acids on downey mildew in cucumber and melon plants were studied. The results, which appear in Table 6, show the good protection given by BABA.

EXAMPLES 13–15:

Following the above described methods, the effect of R-BABA and S-BABA against *Peronospora parasitica* and *Alternaria brassicicola* in broccoli, kohlrabi, and cauliflower were studied; and the results, which appear in Tables 7–9, respectively, show the good protection given by R-BABA.

TABLE 4

The effect of aminobutyric acids on systemic downy mildew of sunflowers (cv. D.I . - 3) caused by *Plasmopara halstedii.*

| Compound | Method of Application | Conc. | Percent Protection |
| --- | --- | --- | --- |
|  |  | 18/21 mg/l |  |
| AABA | spray | 2000 | 10 |
| BABA | spray | 2000 | 100 |
| GABA | spray | 2000 | 0 |
|  |  | mg/Plant |  |
| AABA | soil drench | 5 | 0 |
| BABA | soil drench | 5 | 100 |
| GABA | soil drench | 5 | 0 |
| AABA | root uptake | 2 | 0 |
| BABA | root uptake | 2 | 100 |
| GABA | root uptake | 2 | 0 |

In all experiments inoculation with the fungus was done either 1 day before treatment (curative) or 2 days after treatment.

TABLE 5

The effect of aminobutyric acids on downy mildew caused by *Plasmopara viticola* in grape plants (cv. Sauvignon blanc or Cabernet sauvignon)

| Conc. | Application | % protection with | | |
| --- | --- | --- | --- | --- |
| ppm | mode | AABA | BABA | GABA |
| 10 mg per plant | soil drench | 0 | 60 | 0 |
| 100 | spraying | 0 | 30 | 0 |
| 200 | intact | 0 | 60 | 0 |
| 500 | plants | 15 | 90 | 5 |
| 1000 | in pots | 20 | 95 | 5 |
| 10 |  | 0 | 90 | 0 |
| 50 | floating | 5 | 95 | 0 |
| 100 | leaf discs | 10 | 100 | 5 |

Disease rating was taken 9 days after inoculation. BABA has also curative effect as follows: When applied to inoculated leaf discs at 0, 1, 2 and 3 days after inoculation percent protection was 100, 86, 50 and 30 percent, respectively.

TABLE 6

The effect of aminobutyric acids on downy mildew caused by *Pseudoperonospora cubensis* in cucumber and melon plants (foliar spray) or leaf discs (floating)

| Plant & cultivar | Conc. ppm | AABA | BABA | GABA |
| --- | --- | --- | --- | --- |
|  |  | Percent protection by whole plants | | |
| cucumber | 250 | 0 | 0 | 0 |
| (Dlila) | 500 | 0 | 38 | 0 |
|  | 1000 | 0 | 65 | 0 |
|  | 2000 | 5 | 87 | 0 |
| melon | 250 | 0 | 30 | 0 |
| (Galia) | 500 | 0 | 38 | 0 |
|  | 1000 | 0 | 86 | 0 |
|  | 2000 | 0 | 92 | 0 |

TABLE 6-continued

The effect of aminobutyric acids on downy mildew caused
by *Pseudoperonospora cubensis* in cucumber and melon
plants (foliar spray) or leaf discs (floating)

| Plant & cultivar | Conc. ppm | AABA | BABA | GABA |
|---|---|---|---|---|
| | | leaf discs | | |
| cucumber | 6 | 0 | 94 | 0 |
| (Dlila) | 12 | 0 | 97 | 0 |
| | 25 | 0 | 100 | 20 |
| | 50 | 0 | 100 | 60 |
| melon | 6 | 0 | 19 | 0 |
| (Ananas) | 12 | 0 | 25 | 0 |
| | 25 | 0 | 70 | 0 |
| | 50 | 37 | 85 | 30 |

Disease rating was taken 7 days after inoculation.

TABLE 7

(Broccoli)
Protection of (cv. Shugon) against *Peronospora parasitica* and *Alternaria brassicicola* with amino butyric acids applied as a foliar spray.

| Compound | Conc. ppm | percent protection P. parasitica | A. brassicicola |
|---|---|---|---|
| | 125 | 33 | 0 |
| | 250 | 50 | 20 |
| R-BABA | 500 | 95 | 60 |
| | 1000 | 100 | 85 |
| | 2000 | 100 | 90 |
| | 500 | 0 | |
| S-BABA | 1000 | 0 | not tested |
| | 2000 | 0 | |

TABLE 8

(Kohlrabi)
Protection of (cv. White Wien) against *Peronospora parasitica* and *Alternaria brassicicola* with amino butyric acids applied as a foliar spray.

| Compound | Conc. ppm | percent protection P. parasitica | A. brassicicola |
|---|---|---|---|
| R-BABA | 125 | 33 | 0 |
| | 250 | 50 | 20 |
| | 500 | 95 | 60 |
| | 1000 | 100 | 85 |
| | 2000 | 100 | 90 |
| | 500 | 0 | |
| S-BABA | 1000 | 0 | not tested |
| | 2000 | 0 | |

TABLE 9

Protection of Cauliflower (cv. Nurit) against *Peronospora parasitica* and *Alternaria brassicicola* with amino butyric acids applied as a foliar spray.

| Compound | Conc. ppm | percent protection P. parasitica | A. brassicicola |
|---|---|---|---|
| | 125 | 33 | 0 |
| | 250 | 50 | 20 |
| R-BABA | 500 | 95 | 60 |
| | 1000 | 100 | 85 |
| | 2000 | 100 | 90 |

TABLE 9-continued

Protection of Cauliflower (cv. Nurit) against *Peronospora parasitica* and *Alternaria brassicicola* with amino butyric acids applied as a foliar spray.

| Compound | Conc. ppm | percent protection P. parasitica | A. brassicicola |
|---|---|---|---|
| S-BABA | 500 | 0 | |
| | 1000 | 0 | not tested |
| | 2000 | 0 | |

EXAMPLE 16:

Following the above described methods, the effect of a 25% formulated DL BABA in potatoes was studied. The results are shown in Table 10.

EXAMPLE 17:

Following the above described methods, the markedly good effect of DL-BABA against late blight in potatoes (Bintje) in growth chambers was studied. The results are shown in Table 11.

EXAMPLE 18:

Following the method of Example 16 but running field trials in both Alpha and *Bintje cultivars*, the results are shown in Table 12.

EXAMPLES 19–20:

Resistance to *Peronospora tabacina* induced in tobacco plants was studied as outlined by Y. Cohen (Physiological and Molecular Plant Pathology (1994) 44: 273–88) where the active ingredients were applied as a stem injection or foliar spray. Results are shown in Table 13.

EXAMPLE 21:

Following the method of Examples 19–20, the effect of a soil drench with DL-BABA (3 mg per plant) on blue mold development in tobacco cv. Ky 16 showed an 80 percent control of the disease some 20 days after challenge inoculations.

TABLE 10

EFFECT OF 25% WP FORMULATED DL-BABA IN POTATOES

| ppm DL-BABA | Percent Protection against Phytophthora infections |
|---|---|
| Control | — |
| 31 | 0 |
| 62 | 7 |
| 125 | 67 |
| 250 | 67 |
| 500 | 81 |
| 1,000 | 91 |
| 2,000 | 97 |

TABLE 11

Effect of aminobutyric acids against late blight in potato crops in growth chamber

| Compound | Days after inoculation | Percent blighted leaf area |
| --- | --- | --- |
| Control | 2 | 0 |
|  | 4 | 80 |
|  | 6 | 95 |
|  | 8 | 98 |
|  | 10 | 98 |
| GABA | 2 | 0 |
|  | 4 | 60 |
|  | 6 | 85 |
|  | 8 | 90 |
|  | 10 | 98 |
| DL-AABA | 2 | 0 |
|  | 4 | 45 |
|  | 6 | 70 |
|  | 8 | 80 |
|  | 10 | 98 |
| DL-BABA | 2 | 0 |
|  | 4 | 0 |
|  | 6 | 10 |
|  | 8 | 10 |
|  | 10 | 10 |

TABLE 12

Percentage control of late blight epidemics induced by *Phytophthora infestans* (isolate MR1) in potato crops treated with BABA (25 WP) in three independent field experiments.

| Experiment and cultivar | dose Kg a.i. per ha | Interval between sprays, days 7 | 10 | 14 |
| --- | --- | --- | --- | --- |
| Autumn Alpha | 0 | — | — | 0 |
|  | 0.2 | — | — | 24.6 |
|  | 0.4 | — | — | 52.6 |
|  | 0.8 | — | — | 55.1 |
| Winter Bintje | 0 | 0 | 0 | 0 |
|  | 0.2 | 55.0 | 42.1 | 38.4 |
|  | 0.4 | 57.4 | 52.5 | 47.1 |
|  | 0.8 | 62.6 | 62.6 | 58.0 |
| Spring Alpha | 0 | 0 | — | — |
|  | 0.57 | 38.0 | — | — |
|  | 1.15 | 77.7 | — | — |
|  | 2.30 | 75.0 | — | — |
| Spring Bintje | 0 | 0 | — | — |
|  | 0.57 | 35.2 | — | — |
|  | 1.15 | 64.5 | — | — |
|  | 2.30 | 76.0 | — | — |

TABLE 13

Resistance to *Peronospora tabacina* in tobacco plants by aminobutyric acids

| Compound | Folia Spray (% Protection) | Stem Injection[c] Disease Severity (mean ± SD) |
| --- | --- | --- |
| Water | 0 | 2.0 ± 0a |
| DL-AABA | 10 | 1.3 ± 0.2b |
| DL-BABA | 78 | 0.7 ± 0.2c |
| R-BABA | 99 | 0.07 ± 0.09d |
| GABA | −2 | 2.0 ± 0a |

TABLE 13-continued

Resistance to *Peronospora tabacina* in tobacco plants by aminobutyric acids

| Compound | Folia Spray (% Protection) | Stem Injection[c] Disease Severity (mean ± SD) |
| --- | --- | --- |
| SAa | 80 | 1.5 ± 0b |
| INAb | 61 | 0.5 ± 0c | a Sodium salicylate
b 2,6 dichloro-iso-nicotinic acid
[c]The letters refer to statistics.

EXAMPLE 22:

Sunflower plants were protected against downy mildew caused by *Plasmopora halstedii* by treating the seeds with BABA. Thus, the seeds were soaked for 24 hours in solution containing 10 mg BABA per ml, and then sown in pots in the greenhouse. Two weeks later the developed plants were inoculated with *Plasmopora halstedii*. The progress of the disease was assessed after seven more days with the following results: While the control had 100 percent of the plants remained infected; the treated plants had only a 2 percent rate of infection.

EXAMPLE 23:

Maize (Line 3376) seeds were allowed to sprout in water for 5 days. They were then dipped in a BABA solution for one day. The sprouted seeds were washed and placed in contact with *Fusarium moniliforme* for one day and then planted in pots. After two weeks the progress of the disease was as follows:

| BABA (ppm) | 0 | 125 | 250 | 500 | 2,000 |
| --- | --- | --- | --- | --- | --- |
| Percent plants infected. | 70 | 80 | 40 | 0 | 0 |

EXAMPLE 24:

The activity of N-benzoyl-3-aminobutyric acid n-octyl ester against late blight (*Phytophthora infestans*) on potato in growth chamber was studied. Six week old plants in pots were sprayed with the compounds and inoculated two days later. Disease records taken 7 days post-inoculation are listed in Table 14.

TABLE 14

Activity of N-benzoyl-3-aminobutyric acid n-octyl ester against late blight (Phytophthora infestans) on potato in growth chambers.

| Concentration ppm | % protection |
| --- | --- |
| 500 | 77 |
| 1000 | 89 |
| 2000 | 96 |

EXAMPLE 25:

The effect of BABA against grey mold in tomatoes and cucumbers was studied. Young tomatoes (cultivar Baby) plants (4-leaf stage) and young cucumbers (cultivar Diila) plants (1-leaf stage) were sprayed with BABA and inoculated two days later with spores suspension of *Botrytis cinera*. The plants were kept under a moist Perspex cover in a growth chamber for four days and then monitored for infection. The results are listed in Table 15.

TABLE 15

The effect of BABA against grey mould, incited by *Botrytis cinerea*, in tomato and cucumbers.

| BABA conc | Percent plants infected | |
|---|---|---|
| (ppm) | Tomato | Cucumber |
| 0 | 100 | 100 |
| 62 | 20 | 50 |
| 125 | 0 | 30 |
| 200 | 0 | 0 |
| 500 | 0 | 0 |
| 1000 | 0 | 0 |
| 2000 | 0 | 0 |

What is claimed is:

1. A method for protecting a crop selected from the group consisting of cucumbers, melon, broccoli, cauliflower, kohlrabi, potatoes, sunflower, tobacco, grapes, cotton, maize, sorghum, cabbage, pearl millet, rice and hop, against fungal diseases caused by fungi by inducing local and systemic resistance of said crop, comprising:

applying to the crop or its locus a composition containing an effective amount, sufficient to induce local and systemic resistance of the crop to control the fungal disease, of a compound selected from the group consisting of β-amino butyric acid, R-β-amino butyric acid; D,L-N-benzoyl-3-aminobutyric acid, and β-aminovaleric acid and salts thereof.

2. A method according to claim 1 wherein the compound of formula (I) is R β-aminobutyric acid or β-aminovaleric acid.

3. A method according to claim 1 wherein the crop is selected from the group consisting of sunflower, grapes, cucumber, melon, broccoli, kohlrabi, cauliflower, potatoes, tobacco and maize.

4. A method according to claim 1 wherein the compound is applied to the leaves or stems of the plant.

5. A method according to claim 1 wherein the compound is applied to the roots of the plant.

6. A method according to claim 1 wherein the compound is applied to the soil.

7. A method according to claim 1 wherein the compound is applied to the seeds, tubers, or bulbs of the plant.

8. A method according to claim 1 wherein the compound is applied pre-emergence.

9. A method according to claim 1 wherein the compound is applied post-emergence.

10. A method according to claim 1 wherein the compound is applied to the crop at a dosage rate of from 0.1 to 5 kg/ha.

11. A method according to claim 1 wherein the compound is applied to the crop a dosage rate of 0.2 to 2 kg/ha.

12. A method according to claim 1 wherein said compound is β-aminobutyric acid, or a salt, thereof.

13. A method according to claim 1, wherein said crop is rice.

14. A method for protecting tomatoes against *Fusarium oxysporum* f. sp. *lycopersici* by inducing local and systemic resistance of the the tomatoes, comprising applying to the tomato plant or its locus an effective amount sufficient to induce local and systemic resistance in the crop to control the fungal disease, of a compound selected from the group consisting of β-amino butyric acid, R-β-amino butyric acid; D,L-N-benzoyl-3-aminobutyric acid, and β-aminovaleric acid and salts thereof.

15. A method according to claim 14 wherein the compound is R-β-aminobutyric acid or β-aminovaleric acid.

16. A method according to claim 14 wherein the compound is applied to the leaves or stems of the plants.

17. A method according to claim 14 wherein the compound is applied to the soil.

18. A method according to claim 14 wherein the compound is applied to the soil.

19. A method according to claim 14 wherein the compound is applied to the seeds.

20. A method according to claim 14 wherein the compound is applied post-emergence.

21. A method according to claim 14, wherein said compound is β-aminobutyric acid, or a salt thereof.

22. A method for protecting a crop against grey mould by inducing local and systemic resistance of said crop, comprising:

applying to the crop or its locus an effective amount sufficient to induce local and systemic resistance of the crop to control the fungal disease, of a compound selected from the group consisting of β-amino butyric acid, R-β-amino butyric acid; D,L-N-benzoyl-3-aminobutyric acid, and β-aminovaleric acid and salts thereof.

23. A method according to claim 2 wherein the compound is β-aminobutyric acid.

24. A method according to claim 22 wherein the crop is selected from the group consisting of tomatoes and cucumbers.

25. A method according to claim 22 wherein the composition is applied to the leaves or stems of the plant.

26. A method according to claim 22 wherein the composition is applied to the roots of the plant.

27. A method according to claim 22 wherein the composition is applied to the soil.

28. A method for protecting potatoes against fungal diseases selected from the group consisting of late blight, early blight and leaf spots, by inducing local and systemic resistance of the potato comprising: applying to a potato plant or its locus a composition containing an effective amount of DL-β-aminobutyric acid, R-β-aminobutyric acid, DL-N-benzoyl-3 aminobutyric acid, octyl ester or mixtures thereof.

29. A method according to claim 28 wherein the compound is applied to the leaves or stems of the plant.

30. A method according to claim 28 wherein the compound is applied to the roots of the plant.

31. A method according to claim 28 wherein the compound is applied to the soil.

32. A method according to claim 28 wherein the compound is applied to the tubers, of the plant.

33. A method according to claim 28, wherein said compound is β-aminobutyric acid, or a salt.

34. A method for protecting rice plants against fungal diseases caused by fungi by inducing local and systemic resistance of said rice plant, comprising:

applying to said rice plant or its locus an amount, sufficient to induce local and systemic resistance of the rice plant to control of the fungal disease, of β-aminobutyric acid or a salt thereof.

35. A method according to claim 34, wherein said β-aminobutyric acid is applied to the leaves or stems of the rice plant.

36. A method according to claim 34, wherein said β-aminobutyric acid is applied to the roots of the rice plant plant.

37. A method according to claim 34, wherein said β-aminobutyric acid is applied to the soil.

* * * * *

UNITED STATES PATENT AND TRADEMARK OFFICE
CERTIFICATE OF CORRECTION

| | | |
|---|---|---|
| PATENT NO. : | 5,830,919 | Page 1 of 3 |
| DATED : | Nov. 3, 1998 | |
| INVENTOR(S) : | Yigal Cohen | |

It is certified that error appears in the above-identified patent and that said Letters Patent is hereby corrected as shown below:

On Cover page, under "Other Publications", 6th and 7th lines from the bottom, delete "The American Phytopathological Society, vol. 84, No. 1, 1993" and insert therefor --Phytopathology, vol. 84, No. 1, 1994--.

Column 1, line 26, delete "gluconases" and insert therefor --glucanases--.

Column 1, line 34, after "245704" delete ")".

Column 1, line 50, delete "DL-ßaminobutyric" and insert --DL-ß-isoaminobutyric--.

Column 2, line 32, delete "0Ort" and insert therefor --Oort--.

Column 3, line 26, delete "ß-amino" and insert therefor --α-amino--.

Column 5, line 1, delete "$HC_1CF_3CO_2H$" and insert therefor --$HCl.CF_3CO_2H$--.

UNITED STATES PATENT AND TRADEMARK OFFICE
CERTIFICATE OF CORRECTION

PATENT NO. : 5,830,919
DATED : Nov. 3, 1998
INVENTOR(S) : Yigal Cohen

It is certified that error appears in the above-identified patent and that said Letters Patent is hereby corrected as shown below:

Column 6, line 64, delete "(1)" and insert therefor --(I)--.

Column 8, line 33, delete "seek" and insert therefor --seed--.

Column 9, line 30, delete "3.0r" and insert therefor --3.0 g--.

Column 12, line 11, delete "18/21 mg/l" and insert therefor --mg/l--.

Column 14, line 33, delete "Bintje cultivars" and insert therefor --Bintje cultivars--.

UNITED STATES PATENT AND TRADEMARK OFFICE
CERTIFICATE OF CORRECTION

PATENT NO. : 5,830,919
DATED : Nov. 3, 1998
INVENTOR(S) : Yigal Cohen

It is certified that error appears in the above-identified patent and that said Letters Patent is hereby corrected as shown below:

Column 17, line 31, (claim 1, line 12), delete "D,L-" and insert therefor --DL- --.

Column 18, line 41, (claim 28, line 7), delete "acid,octyl" and insert therefor --acid octyl--.

Signed and Sealed this

Twenty-fifth Day of May, 1999

Attest:

Attesting Officer

Q. TODD DICKINSON

Acting Commissioner of Patents and Trademarks